United States Patent [19]  
Dittman

[11] 4,307,259  
[45] Dec. 22, 1981

[54] PREPARATION OF TETRABROMOTETRACHLOROPERFLUORODODECANES

[75] Inventor: Albert L. Dittman, Allendale, N.J.

[73] Assignee: Halocarbon Products Corporation, Hackensack, N.J.

[21] Appl. No.: 917,145

[22] Filed: Jun. 19, 1978

[51] Int. Cl.³ .............................................. C07C 17/26
[52] U.S. Cl. ................................... 570/125; 570/172; 570/171
[58] Field of Search ............ 204/163 R; 260/653.1 R, 260/653 R; 570/125, 172, 171

[56] References Cited

U.S. PATENT DOCUMENTS 2,705,229  3/1955  Ruh et al. .................. 260/653.1 R
2,783,219  2/1957  Passino et al. ............. 260/653.1 R
3,046,304  7/1962  Haszeldine ................. 260/653.1 R

FOREIGN PATENT DOCUMENTS 729560  5/1955  United Kingdom ......... 260/653.1 R

Primary Examiner—Delbert E. Gantz
Assistant Examiner—Joseph A. Boska
Attorney, Agent, or Firm—Sprung, Felfe, Horn, Lynch & Kramer

[57] ABSTRACT

A substantially pure mixture of tetrabromotetrachloroperfluorododecanes of the empirical formula $C_{12}Br_4Cl_4F_{18}$, of which the isomer

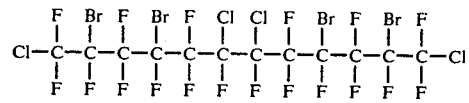

is a significant part, is prepared by oligomerizing bromotrifluoroethylene in the presence of chlorine and distilling, thereby obtaining a substantially pure mixture of trimers of the empirical formula $C_6Br_3Cl_2F_9$, of which the isomer

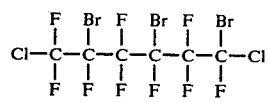

is a significant part and reacting the trimer mixture with zinc in the presence of acetic anhydride to form a perhalododecane. The product is especially useful as a gyroscopic flotation fluid because of its stability, homogeneity and density.

2 Claims, No Drawings

PREPARATION OF TETRABROMOTETRACHLOROPERFLUORODODECANES

The present invention relates to the preparation of a substantially pure mixture of perhalogenated dodecanes containing fluorine, chlorine and bromine atoms.

Perhaloalkanes are used as inert liquid media for a variety of purposes, e.g. gyroscopic flotation fluids, and the like. These materials are usually prepared by oligomerization of perhaloolefins, resulting in a mixture of compounds of varied degrees of polymerization. While the dimers, trimers and tetramers can often be separated by distillation, the higher oligomers are not sufficiently volatile for separation in this manner. This is unfortunate, however, since such higher molecular weight materials are most useful for certain applications precisely because of their stability, non-volatility and high viscosity.

However, for maximum efficiency it is desirable if for any given application there were employed a material of uniform composition as, for example, a pure compound or a mixture of isomers. Thus, if there were a slight loss of material due to volatilization the composition still would not change; similarly the density and other properties would not change under the circumstances where an inhomogeneous material would. An example of such a phenomenon is the thermal diffusion process. If an inhomogeneous liquid is exposed to a hot surface on one side and a cold one on the other, the lower molecular weight components will rise and the higher ones will fall. Thus, the properties of the liquid, i.e. density, will be different in various locations of the liquid from the original values. A homogeneous material or a mixture of isomers cannot undergo this change. Not only does this mean measurements of gyroscopic instruments would be true even after partial loss or in the presence of thermal diffusion conditions but make-up liquid of the same composition can readily be added with assurance that there is no continuous drift in composition.

At JACS Vol. 75 (1953) page 5750 Henne discloses production of a perhalohexane by reaction of a perhalopropane with zinc in the presence of acetic anhydride. An attempt to produce n-octane from butyl bromide in similar manner proved unsuccessful and no products with more than six carbon atoms were produced. Such low molecular weight products, however, can be produced by other processes and readily purified by distillation.

In a later article of JACS Vol. 76 (1953) pages 1175-6 Henne et al correct some mistakes in the earlier work about the intermediates and produce mono- and di-olefins by dehydrohalogenation with zinc. Again, however, their work was limited to products with six carbon atoms and the purpose of the work was solely to ascertain the direction of free radical addition of $CF_2=CFCl$.

It is accordingly an object of the present invention to provide one commercially useful particular perhalododecane of substantial purity, low volatility and marked stability.

This and other objects and advantages are realized in accordance with the present invention pursuant to which there is provided a substantially pure mixture of isomers of tetrabromotetrachloroperfluorododecane of the formula $C_{12}Br_4Cl_4F_{18}$, of which the isomer

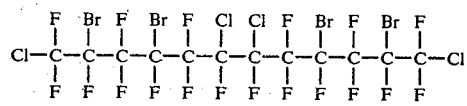

is a significant part and a process for its preparation. Specifically, bromotrifluoroethylene, $CF_2=CFBr$, is polymerized in known manner to produce a product containing a mixture of trimers, although there are significant amounts of other oligomers present. This mixture is subjected to distillation to recover a cut which is a substantially pure mixture of $C_6Br_3Cl_2F_9$, containing a significant amount of

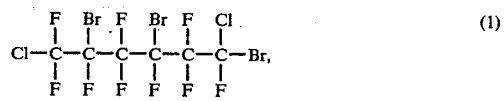

since the boiling point of the mixture of isomers is significantly different from that of the corresponding dimers and tetramers. Other trimers which are believed to be present include $CF_2ClCFBrCF_2CFBrCFBrCF_2Cl$ (2)

$CFBrClCF_2CF_2CFBrCF_2CFBrCl$ (3)

$CF_2ClCFBrCFBrCF_2CF_2CFBrCl$ (4)

Then the mixture of trimers is mixed with zinc which reacts with those isomers which contain the bromochlorofluoromethyl end groups, i.e. trimers (1), (3) and (4), but not (2). The bromine atom which is on the carbon atom with chlorine and fluorine is removed from two different molecules by the zinc and the bromine-free ends are coupled. This is illustrated below using two molecules of the more significant isomer:

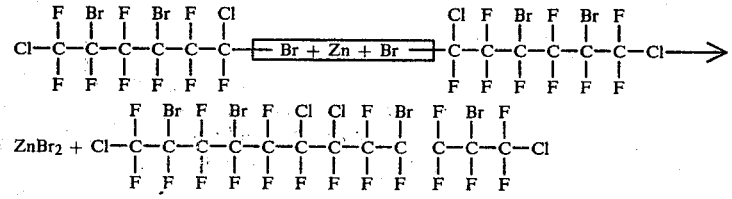

Other dodecanes which can be formed by interaction of a trimer molecule of (1) with (3), (1) with (4), (3) with (3), (4) with (4) and (3) with (4) are $CF_2ClCFBrCF_2CFBrCF_2CFClCFClCF_2CF_2CFBrCF_2CFBrCl$ $CF_2ClCFBrCF_2CFBrCF_2CFClCFClCF_2CFBrCF_2CFBrCl$ $CF_2ClCFBrCF_2CFBrCF_2CFClCFClCF_2CF_2CFBrCFBrCF_2Cl$ $CF_2ClCFBrCFBrCF_2CF_2CFClCFClCF_2CF_2CFBrCF_2CFBrCl$ $CF_2ClCFBrCFBrCF_2CF_2CFClCFClCF_2CF_2CFBrCF_2CFBrCl$ $CFBrClCF_2CF_2CFBrCF_2CFClCFClCF_2CFBrCF_2CFBrCl$ $CFBrClCF_2CFBrCFBrCF_2CFClCFClCF_2CF_2CFBrCF_2CFBrCl$ $CFBrClCF_2CFBrCF_2CF_2CFClCFClCF_2CF_2CFBrCF_2CFBrCl$ $CF_2ClCFBrCFBrCF_2CF_2CFClCFClCF_2CF_2CFBrCFBrCF_2Cl$ Advantageously the zinc dimerization can be effected in the presence of an inert solvent. As a solvent and promoter to activate zinc, acetic anhydride as a reaction medium has also proven particularly effective and it may be used in molar amounts ranging from about 1 to 10 times and preferably about 2 to 4 times the zinc. The reactants are combined with cooling, advantageously to about 0° C. or lower, e.g. about −20° C., and held until the zinc has all reacted, the temperature thereafter being permitted to rise gradually to about room temperature, although elevated temperature, e.g. about 60° C., may be utilized. The total reaction time can be, but need not be, several days.

The reaction mass is then treated to recover the desired product. Addition of water serves to dissolve the zinc bromide and form an aqueous layer from which the perhalododecanes can readily be separated. If acetic anhydride is present, it will be hydrolyzed by water and end up in the aqueous layer. If a solvent such as methylene chloride is present it may end up in the organic layer but, because of its volatility, it can readily be distilled off leaving substantially pure homogeneous product.

The invention is further described in the following illustrative example wherein all parts are by weight unless otherwise expressed:

EXAMPLE

Gaseous bromotrifluoroethylene is polymerized at 40° C. in the presence of chlorine and ultraviolet light as catalyst to produce a mixture of oligomers. After treatment to remove unreacted monomer and other unsaturated compounds there is obtained by fractional distillation a substantially pure mixture of trimers, tribromodichlorononafluorohexane boiling at approximately 55° C. at 0.02 mm Hg. This mixture is 99.8% pure by vapor phase chromatography.

To the hexanes in a 500 ml three-neck flask equipped with a thermometer and a mechanical stirrer there are added 400 ml of acetic anhydride per mole of hexane. The mixture is cooled to the desired reaction temperature under a nitrogen atmosphere and then zinc powder is added in approximately the stoichiometric amount. Next, five drops of 70% aqueous zinc chloride solution are added to the flask. The reaction mixture is stirred at a constant temperature until the grey zinc color disappears or there is only a very thin grey haze. Then the mixture is warmed to room temperature over a five-hour period. Six hundred ml of water per mole of hexane is added to the flask over a 30 minute period with stirring and cooling to prevent overheating. The mixture is next heated to 50° C. for one-half hour and then cooled to room temperature. After separating the aqueous layer the lower phase is washed with 5% aqueous NaOH and dried over silica gel. By distillation of the resulting liquid there is first obtained unreacted starting material and low boiling byproducts and then intermediate byproducts. Thereafter a reduction of the pressure, e.g. to about 0.02 mm of Hg, gives the desired product which is collected at elevated temperature, e.g. approximately 110° to 130° C.

The results of runs at different conditions are set forth in the following table:

TABLE 1

| RUN | ZINC REACTION Time Hr. | ZINC REACTION Temp., °C. | DIGESTION Time Hr. | DIGESTION Final Temp. °C. | MOLES STARTING MATERIAL Supplied | MOLES STARTING MATERIAL Recovered | MOLES STARTING MATERIAL Consumed | MOLES PRODUCT | YIELD % | CONV. % |
|---|---|---|---|---|---|---|---|---|---|---|
| 1 | 5 | −4 to −9 | 25 | 55 | 0.375 | 0.172 | 0.203 | 0.0569 | 56.2 | 54.0 |
| 2 | 11 | −7 to −11 | 67 | 22 | 0.407 | 0.173 | 0.234 | 0.0655 | 56.0 | 57.5 |
| 3 | 2.5 | 10 to 15 | 41 | 22 | 0.394 | 0.198 | 0.197 | 0.0467 | 47.5 | 49.9 |
| 4 | 11 | −11 to −14 | 67 | 22 | 0.685 | 0.294 | 0.392 | 0.1153 | 58.9 | 57.1 |
| 5* | 11 | −8 to −12 | 67 | 23 | 0.265 | 0.110 | 0.155 | 0.0410 | 52.8 | 58.6 |

*Starting material was recovered from previous runs.

It will be noted from Table 1 that both the yield and conversion are lower for Run 3 than for any other run. This appears to be related to the higher reaction temperature which resulted in a higher percentage of byproducts accompanied by a greater wasteful consumption of zinc and consequent lower conversion of the starting material. Temperatures below 0° C. are advantageous for this reason but higher temperatures still give a useful product.

Two analyses of the product of Run 1 gave the following results:

TABLE 2

| ELEMENTAL ANALYSIS $C_{12}Br_4Cl_4F_{18}$, molecular weight 947.63 | | | |
|---|---|---|---|
| | | Theory % | Found % |
| $C_{12}$ | 144.12 | 15.12 | 15.25, 15.24 |
| $Br_4$ | 319.68 | 33.73 | 34.56, 34.18 |
| $Cl_4$ | 141.83 | 14.97 | 14.23, 14.05 |
| $F_{18}$ | 342.00 | 36.09 | 35.51, 35.31 |

It will be appreciated that the instant specification and examples are set forth by way of illustration and not limitation, and that various modifications and changes may be made without departing from the spirit and scope of the present invention.

What is claimed is:

1. A substantially pure mixture of isomers of tetrabromotetrachloroperfluorododecane of the empirical formula $C_{12}Br_4Cl_4F_{18}$.

2. A process for producing a mixture according to claim 1, which comprises oligomerizing bromotrifluoroethylene in the presence of chlorine, separating a substantially pure mixture of tribromodichloroperfluorohexanes by distillation, reacting such mixture with zinc at a temperature below about 0° C. in the presence of acetic anhydride, at the end of the reaction adding water in amount sufficient to form an aqueous and an organic layer, removing the aqueous layer, and recovering the desired product from the organic layer by distilling off readily volatile unreacted perhalohexane and by-products.

* * * * *